(12) United States Patent
Vega

(10) Patent No.: US 8,640,708 B2
(45) Date of Patent: Feb. 4, 2014

(54) RESTRAINING GLOVE

(76) Inventor: Maria Y. Vega, San Antonio, TX (US)

(*) Notice: Subject to any disclaimer, the term of this patent is extended or adjusted under 35 U.S.C. 154(b) by 24 days.

(21) Appl. No.: 13/543,558

(22) Filed: Jul. 6, 2012

(65) Prior Publication Data
US 2014/0007889 A1 Jan. 9, 2014

(51) Int. Cl.
A61F 5/37 (2006.01)

(52) U.S. Cl.
USPC .................. 128/878; 602/21; 2/161.4

(58) Field of Classification Search
USPC ............ 602/20–22; 2/161.1, 161.2, 161.3, 2/161.4; 482/55, 105, 157
See application file for complete search history.

(56) References Cited

U.S. PATENT DOCUMENTS

| | | | | |
|---|---|---|---|---|
| 4,746,313 A | * | 5/1988 | Bray et al. ................ | 441/57 |
| 5,468,200 A | * | 11/1995 | Hoffman ................... | 482/55 |
| 5,820,526 A | * | 10/1998 | Hoffman ................... | 482/55 |
| 5,926,847 A | * | 7/1999 | Eibert ...................... | 2/161.2 |
| 6,216,276 B1 | * | 4/2001 | Eibert ...................... | 2/161.2 |
| 6,704,936 B1 | * | 3/2004 | Carlin ...................... | 2/18 |
| 2010/0287720 A1 | * | 11/2010 | Kayata et al. ............. | 15/227 |

* cited by examiner

Primary Examiner — Michael A. Brown
(74) Attorney, Agent, or Firm — The Law Office of Jerry D. Haynes

(57) ABSTRACT

The present invention is a restraining glove that includes a base glove with a mitt portion and a bottom portion, a hook and loop strap with a hook portion and a loop portion and a belt loop disposed on the bottom portion of the base glove. The restraining glove also includes a crease disposed on the hook and loop strap, the crease is accommodated and received by the belt loop when the hook and loop strap is wrapped around the belt strap and a mesh portion that covers the top of the mitt portion of the base glove, the mesh portion provides a high degree of comfort to the user.

20 Claims, 2 Drawing Sheets

RESTRAINING GLOVE

TECHNICAL FIELD & BACKGROUND

Mitt restraints are designed to limit the ability of a user to harm him or herself as well as others. These mitt restraints are frequently utilized in hospitals to prevent people from hurting themselves or other often do to mental illness or other medical condition. However, common restraints include bulky mitts that preclude finger movement.

The present invention generally relates to a pair of gloves. More specifically, the invention is a pair of restraining gloves.

It is an object of the invention to provide a pair of restraining gloves that provides restraint while allowing a user to move their fingers within the gloves.

It is an object of the invention to provide a pair of restraining gloves that provides air flow within the gloves to increase the comfort of the user wearing the gloves.

It is an object of the invention to provide a pair of restraining gloves that prevent pain and discomfort for the user wearing the gloves.

What is really needed is a pair of restraining gloves that provides restraint while allowing a user to move their fingers within the gloves that provides air flow within the gloves to increase the comfort of the user wearing the gloves that prevent pain and discomfort for the user wearing the gloves.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase "in one embodiment" is utilized repeatedly. The phrase generally does not refer to the same embodiment, however, it may. The terms "comprising", "having" and "including" are synonymous, unless the context dictates otherwise.

Figure 1A:
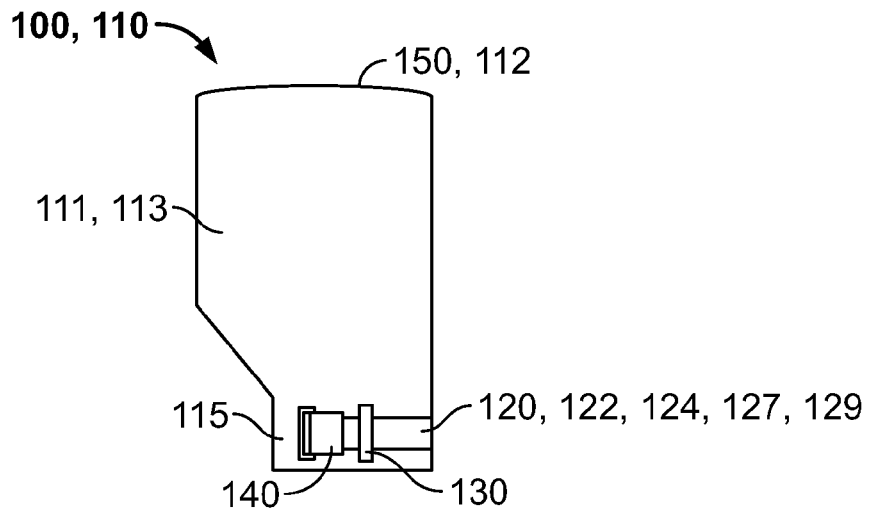
FIG. 1A illustrates a side view of a restraining glove, according to an embodiment of the present invention.

FIG. 1A illustrates a side view of a restraining glove 100, according to an embodiment of the present invention. The restraining glove 100 illustrated in FIG. 1A is in a secured position where the restraining glove 100 is secured around a user's hand and wrist (not shown). The restraining glove 100 provides restraint while allowing a user to move their fingers within the restraining glove 100. The restraining glove 100 provides air flow within the restraining glove 100 to increase the relative comfort of the user wearing the restraining glove 100 that prevents pain and discomfort for the user wearing the restraining glove 100.

The restraining glove 100 includes a base glove 110, a hook and loop strap 120, a belt loop 130, a crease 140 and a mesh portion 150. The base glove 110 has a mitt portion 111 with a general rectangular shape 113 and a bottom portion 115. The mitt portion 111 contains a user's hand and restricts the user's hand while allowing some limited movement of a user's fingers within the mitt portion 111. The bottom portion 115 of the base glove 110 is relatively narrower than the mitt portion 111 and accommodates a user's wrist. The base glove 110 can be made of cotton, denim, rayon or other suitable breathable material to provide a relatively high degree of comfort to the user. The base glove 110 is washable and shrink-free and is approximately 13 inches in height and 10 inches in width, but can be other suitable dimensions as well. The hook and loop strap 120 has a hook portion 122 and a loop portion 124 where the hook and loop fastener 120 is attached to the base glove 110.

The belt loop 130 is disposed on the bottom portion 115 of the base glove 110. The hook and loop strap 120 is inserted through and wrapped around the belt loop 130. The crease 140 is disposed on the hook and loop strap 120 and is accommodated and received by the belt loop 130 when the hook and loop strap 120 is wrapped around the belt strap 120. The hook portion 122 of the hook and loop strap 120 can be releasably attached to the loop portion 124 of the hook and loop strap 120 by simple contact of the loop 130. The hook portion 122 of the hook and loop strap 120 is disposed on a first side 127 of the hook and loop strap 120 and the loop portion 124 is disposed on a second side 129 of the hook and loop strap 120. The crease 140 is disposed between the first side 127 of the hook and loop strap 120 and the second side 129 of the hook and loop and pressure, thereby securing the restraining glove 100 around the user's wrist. The hook portion 122 of the hook and loop strap 120 can be releasably pulled and separated from the loop portion 124 of the hook and loop strap 120 typically by hand to release the hook and loop strap 120. A u-shaped opening (FIG. 1C, 145) is formed when the hook portion 122 of the hook and loop strap 120 can be releasably attached to the loop portion 124 of the hook and loop strap 120, thereby allowing the user's wrist to move and flex freely. The mesh portion 150 covers the top 112 of the mitt portion 111 of the base glove 110 to provide a relatively high degree of comfort to the user by allowing a top to bottom flow of air to flow within the restraining glove 100. The mesh portion 150 covers the base glove 110 is waterproof and washable and also provides an aesthetical appeal to the restraining glove 100.

Figure 1B:
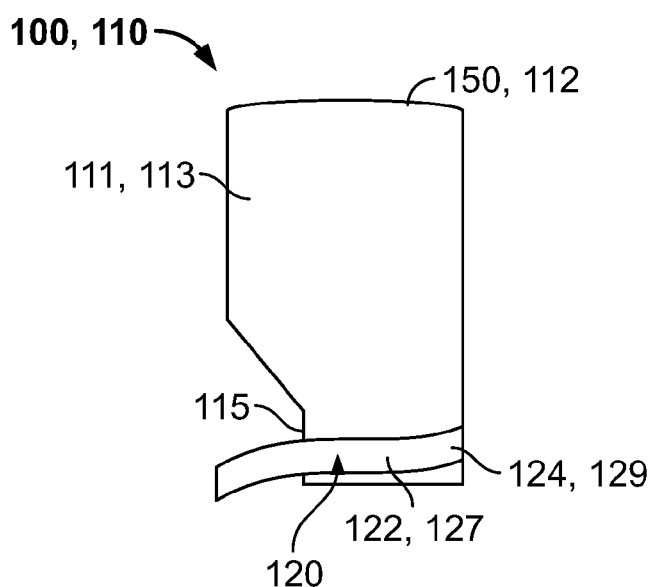
FIG. 1B illustrates a side view of a restraining glove, according to an embodiment of the present invention.

FIG. 1B illustrates a side view of a restraining glove 100, according to an embodiment of the present invention. The restraining glove 100 illustrated and described in FIG. 1B has similar components to the restraining glove 100 illustrated and described in FIG. 1A and its description. These elements include a similar base glove 110, hook and loop strap 120, belt loop 130, crease 140, mesh portion 150 and all of their auxiliary components. FIG. 1B illustrates the restraining glove 100 in an unsecured position in contrast to FIG. 1A which illustrates and describes the restraining glove 100 in a secured position.

Figure 1C:
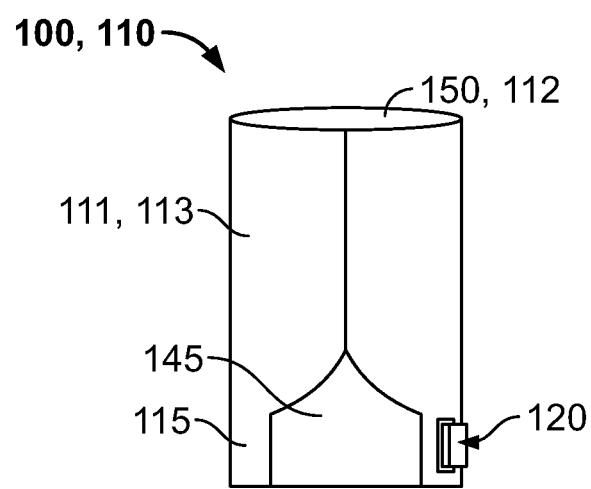
FIG. 1C illustrates a rear view of a restraining glove, according to an embodiment of the present invention.

FIG. 1C illustrates a rear view of a restraining glove 100, according to an embodiment of the present invention. The restraining glove 100 illustrated and described in FIG. 1C has similar components to the restraining glove 100 illustrated and described in FIG. 1A and FIG. 1B and its description. These elements include a similar base glove 110, hook and loop strap 120, belt loop 130, crease 140, mesh portion 150 and all of their auxiliary components. In contrast to FIG. 1A and FIG. 1B, FIG. 1C illustrates the u-shaped opening 145 formed when the hook portion 122 of the hook and loop strap 120 can be releasably attached to the loop portion 124 of the hook and loop strap 120, thereby allowing the user's wrist to move and flex freely.

The restraining glove is a restraining item which allows individuals to move their fingers freely from within the restraining gloves. The restraining gloves are a relatively superior alternative to similar traditional restraining glove products. The restraining gloves fit around a wrist of a user in an open U-shape. As the glove strap at the base of the restraining gloves are tightened, the U-shaped portion begins to close around the fingers of the user, limiting their ability to use their fingers outside of the confines of the mitt, while still allowing movement within the restraining gloves and air flow from the top to the bottom of the restraining glove. Among those who will find the restraining gloves both practical and convenient are nursing homes, hospitals, mental institutions and other suitable facilities. The restraining gloves feature a padded mitt which fastens around the wrist of the user through use of a hook and loop fastener strap and a buckle, providing a relatively strong hold and a relatively high degree of comfort. The restraining gloves are readily available in a variety of colors, thicknesses and materials.

While the present invention has been related in terms of the foregoing embodiments, those skilled in the art will recognize that the invention is not limited to the embodiments described. The present invention can be practiced with modification and alteration within the spirit and scope of the appended claims. Thus, the description is to be regarded as illustrative instead of restrictive on the present invention.

The invention claimed is:

1. A restraining glove, comprising:
   a base glove with a mitt portion and a bottom portion, said mitt portion contains a user's hand and restricts said user's hand while allowing some limited movement of a user's fingers within said mitt portion;
   a hook and loop strap with a hook portion and a loop portion, said hook and loop strap is attached to said base glove;
   a belt loop disposed on said bottom portion of said base glove;
   a crease disposed on said hook and loop strap, said crease is accommodated and received by said belt loop when said hook and loop strap is wrapped around said belt strap; and
   a mesh portion that covers said top of said mitt portion of said base glove, said mesh portion provides a high degree of comfort to said user.

2. The restraining glove according to claim 1, wherein said mitt portion has a general rectangular shape.

3. The restraining glove according to claim 1, wherein said bottom portion is narrower than said mitt portion, said bottom portion accommodates a user's wrist.

4. The restraining glove according to claim 3, wherein said hook and loop strap secures said restraining glove around said user's wrist.

5. The restraining glove according to claim 3, wherein a u-shaped opening is formed when said hook portion of said hook and loop strap is releasably attached to said loop portion of said hook and loop strap, said u-shaped opening allows said user's wrist to move and flex freely.

6. The restraining glove according to claim 1, wherein said base glove is made of cotton.

7. The restraining glove according to claim 6, wherein said base glove is made of denim.

8. The restraining glove according to claim 1, wherein said base glove is made of rayon.

9. The restraining glove according to claim 1, wherein said base glove is washable.

10. The restraining glove according to claim 1, wherein said base glove is shrink-free.

11. The restraining glove according to claim 1, wherein said base glove is approximately 13 inches in height and 10 inches in width.

12. The restraining glove according to claim 1, wherein said hook and loop strap is inserted through and wrapped around said belt loop.

13. The restraining glove according to claim 12, wherein said hook portion of said hook and loop strap is releasably attached to said loop portion of said hook and loop strap by contact and pressure on said loop portion.

14. The restraining glove according to claim 13, wherein said hook portion of said hook and loop strap is disposed on a first side of said hook and loop strap.

15. The restraining glove according to claim 13, wherein said loop portion of said hook and loop strap is disposed on a second side of said hook and loop strap.

16. The restraining glove according to claim 15, wherein said crease is disposed between said first side of said hook and loop strap and said second side of said hook and loop strap.

17. The restraining glove according to claim 1, wherein said hook portion of said hook and loop strap is releasably pulled and separated from said loop portion of said hook and loop strap to release said hook and loop strap.

18. The restraining glove according to claim 1, wherein said mesh portion allows a top to bottom flow of air to flow within said restraining glove.

19. The restraining glove according to claim 1, wherein said mesh portion is waterproof and washable.

20. The restraining glove according to claim 1, wherein said mesh portion provides an aesthetical appeal to said restraining glove.

* * * * *